United States Patent [19]
Borovsky et al.

[11] Patent Number: 5,459,130
[45] Date of Patent: Oct. 17, 1995

[54] METHODS AND COMPOSITIONS FOR THE CONTROL OF THE FLESH FLY

[75] Inventors: Dov Borovsky, Vero Beach, Fla.; Arnold De Loof, Leuven; Dany Bylemans, Leopoldsburg, both of Belgium

[73] Assignee: University of Florida Research Foundation, Inc., Gainesville, Fla.

[21] Appl. No.: 192,243

[22] Filed: Feb. 7, 1994

[51] Int. Cl.$^6$ ............... A61K 38/00; C07K 1/00; C07K 2/00; C07H 19/00
[52] U.S. Cl. ............ 514/17; 530/329; 536/22.1; 536/23.1; 536/23.5
[58] Field of Search ............... 530/329; 514/17; 435/69.1

[56] References Cited

U.S. PATENT DOCUMENTS 5,011,909  4/1991  Borovsky et al. .

OTHER PUBLICATIONS

Borovsky, Dov et al. (1985) "Juvenile Hormone and 20-Hydroxyecdysone as Primary and Secondary Stimuli of Vitellogenesis in Aedes aegypti" Arch. Insect Biochem. Physiol. 2:75–90.
Borovsky, Dov et al. (1990) "Mosquito oostatic factor: a novel decapeptide modulating trypsin-like enzyme biosynthesis in the midgut" FASEB Journal 4:3015–3020.
Borovsky, Dov et al. (1992) "In vivo and In vitro Biosynthesis and Metabolism of Methyl Farnesoate, Juvenile Hormone III, and Juvenile Hormone III Acid in the Mosquito Aedes aegypti" J. Med. Ent. 29:619–629.
Borovsky, Dov et al. (1992) "Development of Specific RIA and ELISA to Study Trypsin Modulating Oostatic Factor in Mosquitoes" Arch. Insect. Biochem. Physiol. 21:13–21.
Borovsky, Dov et al. (1993) "Mass Spectrometry and Characterization of Aedes aegypti Trypsin Modulating Oostatic Factor (TMOF) and its Analogs" Insect Biochem. Mol. Biol. 27:703–712.
Woodhead, A. P. et al. (1989) "Primary Structure of Four Allatostatins: Neuropeptide Inhibitors of Juvenile Hormone Synthesis" Proc. Natl. Acad. Sci. USA 86:5997–6001.
Girardie, Josiane et al. (1989) "Amino Acid Sequence of Locust Neuroparsins" FEBS Letters 245:4–8.
Goltzene, Francine et al. (1978) "The Follicle Cell Epithelium of Maturing Ovaries of Locusta Migratoria: A New Biosynthetic Tissue for Ecdysone" Hoppe-Seyler's Z. Physiol. Chem. 359: 1427–1434.
Hagedorn, H. H. et al. (1975) "The Ovary as a source of α–ecdysone in an Adult Mosquito" Proc. Natl. Acad. Sci. USA 72:3255–3259.
Hanaoka, K. et al. (1980) "Brain Hormone Control of Ecdysone Secretion by the Ovary in a Mosquito" Elsevier/North Holland Biomedical Press 467–479.
Huybrechts, R. et al. (1977) "Induction of Vitellogenin Synthesis in Maile Sarcophaga Bullata By Ecdysterone" J. Insect Physiol. 23:1359–1362.
Bylemans et al. Regulatory Peptide 50(1) pp. 61–72 1994 (Abstract only).
Borovsky et al. The FASEB Journal vol. 4 pp. 3015–3020 Sep., 1990.

Primary Examiner—Robert A. Wax
Assistant Examiner—Hyosuk Kim
Attorney, Agent, or Firm—Saliwanchik & Saliwanchik

[57] ABSTRACT

The subject invention concerns novel peptides which have the property of interfering with the biosynthesis of the enzyme trypsin and the biosynthesis of the hormone ecdysone. This property enables the use of these peptides to, for example, inhibit the formation of progeny in blood-ingesting insects, e.g., Neobellieria, since trypsin is an essential enzyme for food digestion which provides the essential building blocks for egg development in such insects.

9 Claims, 7 Drawing Sheets in vivo conc. of synthetic TMOF (—log M)

METHODS AND COMPOSITIONS FOR THE CONTROL OF THE FLESH FLY

BACKGROUND OF THE INVENTION

In the grey flesh fly, *Neobellieria bullata,* vitellogenesis is cyclic. The repeated gonadotropic cycles suggest that egg development is under hormonal regulation. Previously, it has been shown that egg development in flies and mosquitoes is regulated by ecdysone and juvenile hormone (Huybrechts and De Loof, 1977, 1981; Hagedorn et al., 1975; Borovsky et al. 1985), which are synthesized by the ovary (Goltzene et al. 1978; Hagedorn et al. 1975; Borovsky et al. 1992a, 1992b, 1993d). Neurosecretory cells in the brain usually produce peptide hormones. Two of these peptides, EDNH and allatostatin, control the synthesis of ecdysone and juvenile hormone (Hanaoka and Hagedorn, 1980; Woodhead et al., 1989). In addition, a 65-amino acid peptide, ovary maturing parsin, which acts as a true gonadotropin and stimulates vitellogenin biosynthesis has been recently isolated from the brain of *Locusta migratoria* (Girardie et al. 1991).

Less information is available about the signals that terminate vitellogenesis. An oostatic factor synthesized by the mosquito ovary was recently purified and sequenced from female *Aeries aegypti* (Borovsky et al. 1990, 1993a). The factor, which is a decapeptide, was named Trypsin Modulating Oostatic Factor (TMOF), and its amino acid sequence was determined as $NH_2$-YDPAPPPPPP-COOH (See U.S. Pat. No. 5,011,909). However, this peptide was not found in Neobellieria. We found a completely different hormone in Neobellieria.

BRIEF SUMMARY OF THE INVENTION

The subject invention concerns a novel peptide hormone synthesized by and isolated and purified from the ovaries of the grey flesh fly *Neobellieria* (Sarcophaga) *bullata*. The subject peptide is useful for inhibiting digestion in pests, thus causing sterility (inhibition of egg development) in a treated pest. The isolated and purified compounds of the subject invention are white powders that are highly soluble in water. They can be synthesized on a commercial peptide synthesizer.

More specifically, a preferred embodiment of the invention is a hexapeptide from Neobellieria ovaries, which is the trypsin modulating oostatic factor designated as Neb-TMOF. The subject peptide has the sequence $NH_2$-NPTNLH-COOH (SEQ ID NO. 1). Due to the small size of the subject peptide, it can transverse the gut into the hemolymph much faster than the mosquito factor, which has ten amino acids. The site of action of these factors is a midgut receptor on the hemolymph side. The factor is active at physiological concentrations with an effective dose of 50% inhibition ($ED_{50}$) of trypsin biosynthesis at $10^{-9}$M.

Another object of the subject invention is the commercial use of this peptide to inhibit digestion in flies and other insects. Specifically, the novel factor inhibits trypsin biosynthesis in the midgut by signalling the midgut cells to stop trypsin biosynthesis after food has been digested. Food digestion in the female fly is essential for the development of the oocytes (eggs) in the ovary. Without food, or if the female fly does not synthesize trypsin after the meal, no eggs will be synthesized in the ovary and female fly is essentially sterile. Female flesh flies fed a protein meal and then injected with the novel factor showed, after 24 hours, 50% to 80% lower trypsin biosynthesis than did control female flesh flies injected with saline.

Following this observation we isolated Neb-TMOF from 10,000 ovaries, purified the hormone, and sequenced it. The purified hexapeptide, at physiological concentrations of $10^{-9}$M, inhibited 50% of trypsin biosynthesis in the midgut of female *Neobellieria bullata*. Injection of the hormone also inhibited egg yolk synthesis because the amino acids that are needed for the synthesis were not available when digestion stopped. In addition to its inhibitory effects on trypsin synthesis in the gut, Neb-TMOF is also a potent inhibitor ($EC_{50}=5\times10^{-9}$) of the biosynthesis of ecdysone by ring glands of the flesh flies Neobellieria and Calliphora. "$EC_{50}$" is recognized in the art to mean the "effective concentration, 50% inhibition," i.e., the concentration at which 50% inhibition is effected. The peptide is also present in larval instars. Accordingly, another object of the invention concerns the use of the novel peptide as an inhibitor of ecdysone biosynthesis. Ecdysone is a hormone found in flies and mosquitoes which regulates molting, growth, and gametogenesis. Thus, Neb-TMOF falls into a new class of biorational insecticides that are, advantageously, natural, target-specific, and, in contrast to the early organic insecticides, e.g., DDT, readily degraded in the environment and do not cause pollution problems.

Also included in this invention are addition salts, complexes, or prodrugs such as esters of the peptides of this invention, especially the nontoxic pharmaceutically or agriculturally acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The formulas have weak acidic groups (carboxyl groups); thus, esterification at these groups to form derivatives such as the methyl or ethyl esters, can be prepared by standard procedures. The term "prodrug" is understood in the art to mean a compound chemically related to the subject compound that is converted into the subject compound by metabolic process within the body (biotransformation).

In a further embodiment, the N-terminus and C-terminus of the peptides can be blocked to further inhibit proteolysis by metabolic enzymes. Derivation of peptides to block the N-terminus or C-terminus is known in the art. For example, the N-terminus can be acetylated by methods known to those of ordinary skill in the art; the C-terminus can be amidated as is well known in the art.

The novel peptides can also be synthesized wherein at least one of the amino acids is in the D-conformation, as opposed to the naturally occurring L-rotation conformation. The presence of D-conformation amino acids can inhibit the ability of proteases to degrade the peptides of the Subject invention.

Also, derivation of these compounds with long chain hydrocarbons will facilitate passage through the cuticle into the pest body cavity. Therefore, a further embodiment of the subject invention pertains to compositions comprising the peptides bound to lipids or other carriers.

A further aspect of the subject invention pertains to nucleic acid, e.g., DNA, sequences encoding the peptides disclosed herein. These DNA sequences can easily be synthesized by a person skilled in the art. The sequences may be used to transform an appropriate host to confer upon that host the ability to express the novel peptides. Hosts of particular interest include bacteria, yeasts, insect viruses, and plants. For each of these hosts, the DNA sequences may be specifically designed by a person skilled in the art to utilize codons known to be optimally expressed in the particular hosts. Advantageous promoters can also easily be utilized. Bacteria, yeasts, and viruses each may be used to produce peptide for further use, or these hosts can be used as vehicles for direct application of the peptide to the target pest. Plants can be transformed so as to make the plant effective in controlling or killing a target pest species which feeds on that plant. Methods for transforming plant cells utilizing, for example agrobacteria or viruses, are well known to those skilled in the art.

DETAILED DISCLOSURE OF THE INVENTION

Figure 1:
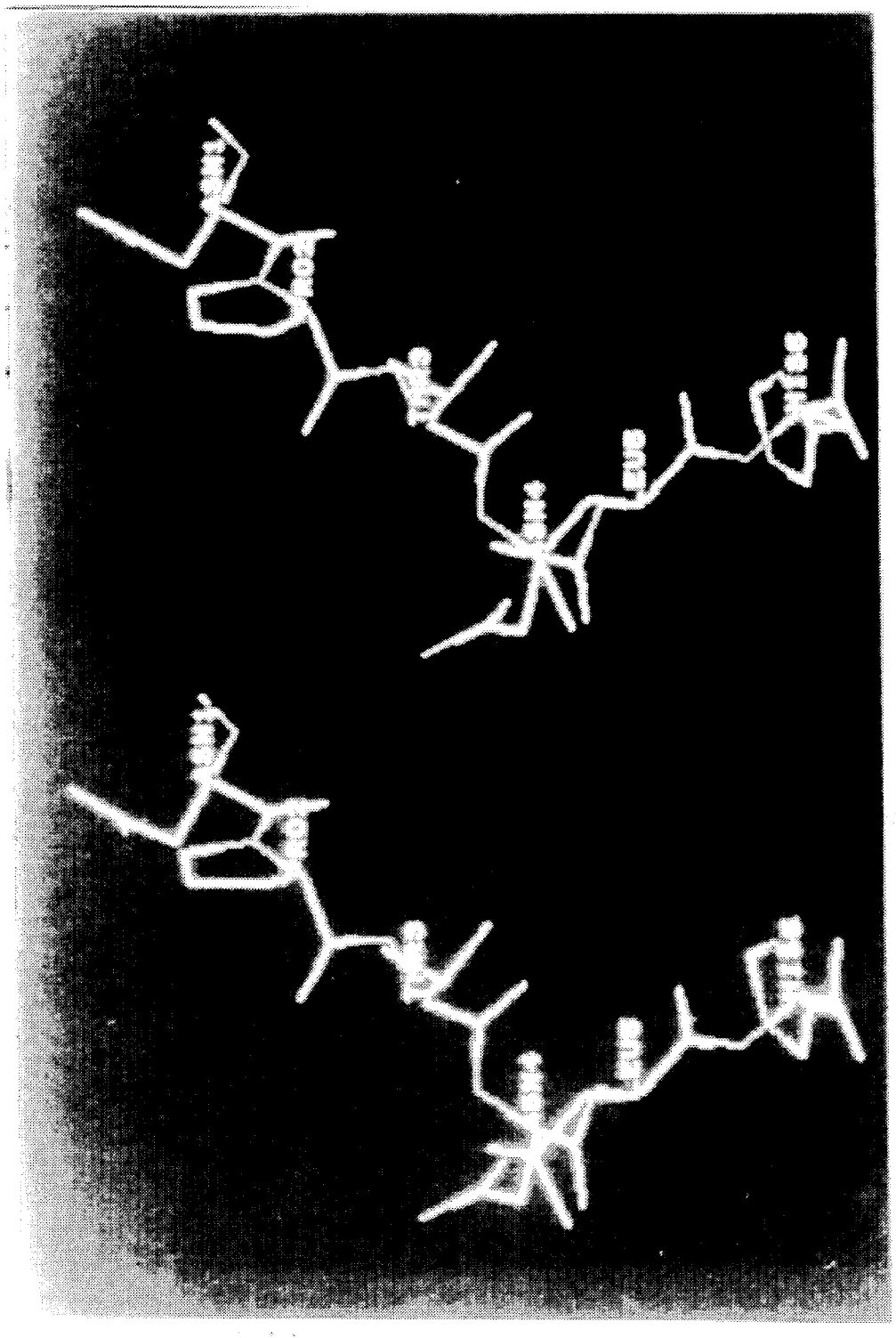
FIG. 1. Stereoview of Neb-TMOF represented by a stick model on a Macintosh II work station connected to a VAX using SYBYL molecular modeling software version 5.2 (Tripos Associates Inc., St. Louis, Mo.). The N-terminus is labeled Asn1 (top) and the C-terminus is His6 (bottom).

The subject invention concerns novel peptides that inhibit digestion in target pests. Specifically exemplified is the use of the peptides with blood-ingesting insects such as the flesh fly (genus Neobellieria). One embodiment of the subject invention is a hexapeptide, designated Neb-TMOF, which has the amino acid sequence shown in SEQ ID NO. 1. Having only six amino acids, it is only about 50% the size of the previously-described TMOF hormone found in mosquitoes. Advantageously, with this substantial truncation as compared to the mosquito factor, the peptide retains biological activity and has important practical advantages because it is rapidly absorbed and less susceptible to proteolysis. Also encompassed within the scope of this invention are certain modifications of these peptides.

The one-letter symbol for the amino acids used herein is well known in the art. For convenience, the relationship of the three-letter abbreviation and the one-letter symbol for amino acids is as follows:

| | | | |
|---|---|---|---|
| Ala | A | Leu | L |
| Arg | R | Lys | K |
| Asn | N | Met | M |
| Asp | D | Phe | F |
| Cys | C | Pro | P |
| Gln | Q | Ser | S |
| Glu | E | Thr | T |
| Gly | G | Trp | W |
| His | H | Tyr | Y |
| Ile | I | Val | V |

The novel peptides of the invention can be prepared by well-known synthetic procedures. For example, the peptides can be prepared by the well-known Merrifield (1963) solid support method. This procedure, though using many of the same chemical reactions and blocking groups of classical peptide synthesis, provides a growing peptide chain anchored by its carboxyl terminus to a solid support, usually cross-linked polystyrene or styrenedivinylbenzene copolymer. This method conveniently simplifies the number of procedural manipulations since removal of the excess reagents at each step is effected simply by washing of the polymer.

Alternatively, these peptides can be prepared by use of well-known molecular biology procedures. Nucleic acid, e.g., DNA, sequences encoding the peptides of the invention can be synthesized readily because the amino acid sequences are disclosed herein. These nucleic acid sequences are a further aspect of the subject invention. These genes can be used to genetically engineer, for example, bacteria, insect or plant viruses, plant cells, or fungi for synthesis of the peptides of the invention.

The insect cell line Sf9 (*Spodoptera frugiperda*), deposit number ATCC CRL 1711, is available from the American Type Culture Collection, 12301 Parklawn Drive, Rockville, Md. 20852 USA. Baculovirus *Autographa californica* nuclear polyhedrosis virus (AcNPV) is available from Texas A&M University, Texas Agricultural Experiment Station, College Station, Tex. 77843, and has been described in Smith and Summers (1978; 1979).

Other nuclear polyhedrosis viruses (See World Health Organization Technical Report No. 531) such as *Spodoptera frugiperda* (Sf MNPV), *Choristoneura furniferana* (Cf MNPV) (Smith and Summers, 1981), or *Spodoptera littoralis* (Sl NPV) (Harrap et al., 1977) can be used instead of *Autographa californica* NPV. Other insect cell lines can also be substituted for *Spodoptera frugiperda* (Sf9), for example, *Trichoplusia ni* (Volkman and Summers, 1975), *Spodoptera exigua*, *Choristoneura furniferana* (Smith and Summers, 1981) and *Spodoptera littoralis* (Harrap et al., 1977).

Viruses can also be used as expression vectors in transfected plant cells, which then produce a desired protein. For example, a heterologous nucleic acid of tobacco mosaic virus (TMV) can be used to express the subject peptide in a plant cell. See Donson et al., 1991. The subject peptide, which is expressed by the virus-transfected plant cell, can be ingested by the target insect pest when the pest feeds on the plant. The ingested peptide can then inhibit production of oocytes in the insect pest as described herein.

The various methods employed in the preparation of the plasmids and transformation of host organisms are well known in the art and are described, for example, in U.S. Pat. Nos. 5,011,909 and 5,130,253. These patents are incorporated herein by reference. These procedures are also described in Maniatis et al., 1982. Thus, it is within the skill of those in the genetic engineering art to extract DNA from microbial cells, perform restrictions enzyme digestions, electrophorese DNA fragments, tail and anneal plasmid and insert DNA, ligate DNA, transform cells, e.g., E. coli or plant cells, prepare plasmid DNA, electrophorese proteins, and sequence DNA.

Treatment by injection of the compounds of the invention into adult female flesh flies after a blood meal stops egg development, thus rendering the female flesh fly sterile and unable to reproduce. Also, using known techniques of molecular biology, fly larvae can be fed genetically engineered bacteria producing oostatic hormone and infect other insect larvae with bacteria or viruses containing the oostatic gene, making them unable to digest their food and subsequently starve to death. A variety of insect viruses, including baculoviruses and entomopoxviruses, are known to those skilled in the art. The production of the claimed peptide compounds by bacteria or virus would be responsible for the starvation activity in larvae and sterilization in adults. This type of treatment of blood-ingesting insect larvae is analogous to the use of bacteria to control insect populations.

In applications to the environment of the target pest, the transformant strain can be applied to the natural habitat of the pest. The transformant strain will grow in the pest upon ingestion, while producing the peptide(s) which will have a deleterious effect on proteolytic enzymes biosynthesis and the ova. The organism may be applied by spraying, soaking, injection into the soil, seed coating, seedling coating or spraying, or the like. Where administered in the environment, concentrations of the organism will generally be from $10^6$ to $10^{10}$ cells/ml, and the volume applied per hectare will be generally from about 0.1 oz. to 2 lbs or more. Where administered to a plant pan inhabited by the target insect, the concentration of the organism will usually be from $10^3$ to $10^6$ cells/$cm^2$.

In aquatic environments, insect control may be attained below the surface by varying the lipid content of the transformant microorganism strain. It is known that indigenous aquatic algae float due to their lipid content. A variation in lipid content will allow the transformant strain to be distributed at desired depths below the water surface.

For commercial formulations, the organisms may be maintained in a nutrient medium which maintains selectivity and results in a low rate of proliferation. Various media may be used, such as yeast extract or L-broth. Once the organism is to be used in the field, the non-proliferating concentrate may be introduced into an appropriate selective nutrient medium, grown to high concentration, generally from about $10^5$ to $10^9$ cells/ml and may then be employed for introduction into the environment of the blood-ingesting insect.

Also, the genetic material of the subject invention, including nucleotide sequences of Neb-TMOF and its various analogs, can be used to transform plants, thereby conferring plant resistance to those plants. Materials and methods for transforming plant cells are well known to those skilled in the art.

The subject Neb-TMOF was purified from Neobellieria using high performance liquid chromatography (HPLC). Preferably, the HPLC procedure for purifying the subject peptide is conducted using five chromatography columns, following preparation of the sample. The in vivo bioassay and the dose-response curve using synthetic Neb-TMOF suggests that it has an important physiological role in directly controlling digestion and indirectly, the female reproductive cycle. Experiments conducted using Neb-TMOF indicated that it is sixfold more active in Neobellieria than the mosquito TMOF. Computer modelling of the subject peptide using the molecular modelling program SYBYL (Tripos Associates, St. Louis Mo. USA) (Borovsky et al. 1993a) showed that the alpha-helix, which is formed by the six consecutive prolines in mosquito TMOF is absent in Neb-TMOF (FIG. 1).

The Neb-TMOF inhibits the de novo biosynthesis of trypsin. Similarly, allatostatins can block juvenile hormone biosynthesis in the corpora allata of the cockroach Diploptera, by inhibiting the biosynthesis of key enzymes in the juvenile hormone biosynthetic pathway. In addition, Neb-TMOF can affect egg development in Neobellieria and Calliphora by inhibiting the biosynthesis of ecdysone.

Materials and Methods

Insect breeding and egg development. Fries were reared as described by Huybrechts and De Loof (1977). During the first three days after adult eclosion flies were fed sugar and water. From the fourth day, flies were fed on slices of beef liver. To maintain a synchronous ovarian development, 2-day-old females were separated and individually caged in plastic tubes, containing wet cotton. At day 4, females were anesthetized with $CO_2$, immediately injected with test peptides in 2 μl of saline and fed liver coated with sugar crystals. The liver-sugar combination attracted the flies resulting in a faster food intake and ovarian development. Oocyte length was measured with an ocular micrometer under a dissecting microscope.

Effect of Neb-TMOF on trypsin biosynthesis. Six hours after injecting Neb-TMOF or analogs, guts were removed and analyzed for trypsin biosynthesis (Borovsky and Schlein, 1988), or kept frozen at −20° C. until use. Trypsin was measured in the presence of [$^3$H]-diisopropylfluorophosphate (DFP) (New England Nuclear, specific activity 10 Ci/mmol). In the presence of serine proteases [$^3$H]DFP is convened into [$^3$H]-diisopropyl phosphoryl- ([$^3$H]DIP) trypsin derivatives which are measured by liquid scintillation. The incubation medium contains 5 mM tosylamide-2-phenylethyl ketone (TPCK) a chymotrypsin inhibitor, thus making the test specific for trypsin. Because the amino acid sequence of Neobellieria trypsin is not known, the term trypsin-like enzyme is more appropriate. However, for reasons of simplicity, the term trypsin is used. Individual guts were homogenized, centrifuged and the supernatant removed and an aliquot (0.1 gut equivalent) was incubated with [$^3$H]DFP for 18 hours at 5° C. Standard curves were obtained with trypsin type III from bovine pancreas (Sigma Chemical Co., St. Louis, Mo.) (Borovsky and Schlein 1988). In each experiment 2 control groups were used: (a) uninjected and, (b) injected with $10^{-7}$M methionine-enkephalin (H-YGGFM-OH), a pentapeptide without an effect on trypsin-like activity. No significant differences were found between the 2 control groups. Statistical significance was calculated using Microstat software. Chymotrypsin-like concentrations were monitored by the same method in the presence of 5 mM tosyl-L-lysine-chloromethyl ketone (TLCK) instead of TPCK to inhibit trypsin-like enzymes (Borovsky and Schlein 1988).

Electrophoresis and fluorography. [$^3$H]DIP-trypsin-like derivatives of 0.04 gut equivalent and 20 μl sample buffer were run by electrophoresis on 12.5% polyacrylamide gel for 1 hour at 20 mA and for 3 hours at 30 mA (Biorad protean 32 CM) (Laemmli, 1970; Borovsky and Schlein, 1988). Gels were stained for 20 minutes with Coomassie Brilliant Blue R250 and destained overnight with methanol/

$H_2O$/acetic acid (40/50/10), and washed 2 times for 30 minutes in 100 ml dimethylsulfoxide (DMSO). Gels were then incubated for 2 h in 200 ml DMSO containing 44 g 2,5-diphenyloxazole (PPO) (Janssen Chimica, Belgium), rinsed with distilled water for 1 hour, dried for 2 hours in a Biorad slab gel dryer at 80° C. and exposed to a Hyperfilm-MP (Amersham) for 2 days at −70° C. Vitellogenin was separated on a 5–15% SDS gradient gel (Huybrechts and De Loof 1977).

Tissue extraction and High Performance Liquid Chromatography. Late vitellogenic ovaries stage 4C (10,000 pairs) were dissected and immediately placed in methanol/water/acetic acid (90:9:1) solution on ice. The ovaries were homogenized, centrifuged for 30 minutes at 9,820 g and 4° C. and sonicated for 2 minutes (MSE Soniprep 150 Sonicator). Methanol was evaporated and the aqueous extract was re-extracted with ethyl acetate and n-hexane. Organic solvents were decanted and the aqueous solution was dried in siliconized round bottom flasks. Extracts were then prepurified on Megabond Elute $C_{18}$ cartridges (Varian). Cartridges were activated with acetonitrile/$H_2O$/trifluoroacetic acid (TFA) (80/19.9/0.1) and afterwards rinsed with aqueous 0.1% TFA. Samples were redissolved in start solution and subsequently eluted with 50% and 80% acetonitrile containing 0.1% TFA. Columns and operation conditions for High Performance Liquid Chromatography (HPLC) on Beckman Programmable Solvent Module 126 connected with a Diode Array Detector Module 168 (Gold system) were:

(i) Deltapak RCM column (25×100 mm) (Waters), solvent A, 0.1% TFA in water; solvent B, 80% acetonitrile in 0.1% aqueous TFA. Column elution conditions: 100% A for 8 minutes, linear gradient to 75% B in 60 minutes, flow rate 8 ml/min.

(ii) Supelco $C_8$ column (4.6×150 mm), cfr. (i) but flow 1.5 ml/min.

(iii) a refilled stainless steel column (4.6×250 mm) with a new phenyl content (Nucleosil 7 C6H5, Machery-Nagel), cfr. (ii).

(iv) cfr. (iii) but A, 0.1% heptafluorobutyric acid (HFBA) and B 80% acetonitrile in 0.1% aqueous HFBA.

(v) cfr. (iii) and (iv), except elution was carried out with 80% acetonitrile in 0.1% aqueous HFBA.

Absorbance was followed at 214 nm. During the first two column procedures, fractions were collected every minute. Afterwards, peaks were collected manually. At each purification step aliquots from each fraction were removed, dried under $N_2$ and rehydrated in HPLC water. Adjacent active fractions were pooled, dried under $N_2$ and redissolved in the buffer used for the next purification step.

Mass and sequence determination. Accurate monoisotopic molecular masses of peptides were obtained by liquid secondary ionization mass spectrometry (LSIMS) on a quadrupole Fourier transform mass spectrometer (QFTMS) constructed in our laboratory and previously described (Hunt et al. 1987). Samples to be analyzed were dissolved in acidic solution, and an aliquot containing 1–10 pmol of peptide was added to a gold-plated, stainless steel, probe tip (2 mm diameter) in addition to 1 µl of matrix (3:1, monothioglycerol:glycerol). The probe tip was then evacuated and inserted into ion source region of the QFTMS. Peptides were sputtered out of the liquid matrix into the gas phase by bombardment of the sample with a pulsed beam of 10 keV $Cs^+$ generated by a cesium ion gun (Antek, Palo Alto, Calif.). This method of ionization (LSIMS) produces a population of singly charged, peptide ions, $(M+H)^+$, characteristic of the peptides in the sample.

Collision activated dissociation (CAD) mass spectra for sequence analysis were recorded on a Finnigan TSQ-70, triple quadrupole mass spectrometer equipped with a Finnigan electrospray ionization source (Finnigan-MAT, San Jose, Calif.). Operation of this instrument has been previously described (Hunt et al. 1986, 1991). Sample aliquots dissolved in acidic solutions were injected into the electrospray ionization source from a fused silica, microcapillary HPLC column with an inside diameter of 75 microns and a length of 70 cm. The last 10 cm of the column was filled with a C-18 packing material. Peptides were eluted at a flow rate of 0.5–1 µl/min with a 10 minute, linear gradient of 0–80% acetonitrile in 0.1M acetic acid. Sequence analysis is conducted routinely at the low to subpicomole level (3-0.3 pmol).

Esterification of the carboxylic acid moieties of peptides was accomplished by the addition of 20–50 µl of 2N methanolic HCl to lyophilized HPLC fractions containing the peptides of interest (Hunt et al. 1986). Esterification proceeded for 90 minutes, and the reagent was removed by vacuum centrifugation of the sample to dryness. Modified peptides were resuspended in an appropriate volume of 5% acetic acid.

N-acetylation of the N-terminus and lysine residues can be performed directly on the microcapillary HPLC column. Peptides were loaded onto the microcapillary column and washed with water for 3 minutes. Reagent, 1 µl acetic anhydride is 100 µl of 200 mM ammonium acetate, pH 8.0, was then loaded onto the column for 3 minutes (one column volume). The column was washed with water again for 3 minutes before starting the HPLC program.

Automated Edman sequencing was performed using an Applied Biosystems (Foster City, Calif.) model 473A pulsed liquid protein sequencer and 120A analyzer operated according to standard procedures.

Peptide synthesis. Peptides were synthesized using solid phase 9-fluoroenylmethoxycarbonyl (Fmoc) methodology. The coupling of the C-terminal amino acid to the resin was catalyzed by 4-dimethylaminopyridine. Chain elongation and coupling of amino acids were done using H-hydroxybenzotriazole-monohydrate. Twenty percent piperidine in dimethylformamide was used to remove the protecting Fmoc group of each amino acid. TFA was used to cleave the peptide and remove protecting group from side chains. The peptide was then dried by rotary evaporation and prepurified on a Sep-Pak column (Waters Associates) using the same conditions for the Megabond Elut column. The synthetic peptide was then repurified on a Waters Superpac Pep S $C_2/C_{18}$ 5 µm column.

Amino acid analysis. The purified synthetic peptide was hydrolyzed with 6N HCl at 120° C. for 18 hours. The amino acid content of the peptide was determined using ion exchange separation on a Kontron Chromakon 400 amino acid analyzer followed by postcolumn derivatization with ninhydrin. Absorbance was followed at 570 nm.

Methyl ester formation. A standard solution of 2N HCl in methanol was prepared by adding 800 µl of acetyl chloride dropwise, with stirring, to 5 ml of methanol. After 5 minutes incubation at room temperature, a 100 µl aliquot of the reagent was added to the lyophilized peptide sample. The sample was esterified for 2 hours at room temperature and the solvent removed by lyophilization.

Peptide N-acetylation. The peptide was dissolved in 50 µl of 50 mM ammonium bicarbonate (pH 8.0) and 50 µl of freshly prepared acetylation reagent was added to this solution. Acetylation reagent was prepared by adding 100 µl of acetic anhydride to 300 μl of dry methanol and lyophilizing the mixture after allowing it to stand 15 minutes. Acetylated peptide was analyzed directly without further purification.

Manual Edman degradation. Manual Edman degradations were performed as previously described (Tarr, 1977) and modified for use with mass spectrometry (Hunt et al., 1986).

Following are examples which illustrate procedures, including the best mode, for practicing the invention. These examples should not be construed as limiting. All percentages are by weight and all solvent mixture proportions are by volume unless otherwise noted.

EXAMPLE 1—Synthesis of Trypsin in the Gut

Figure 2:
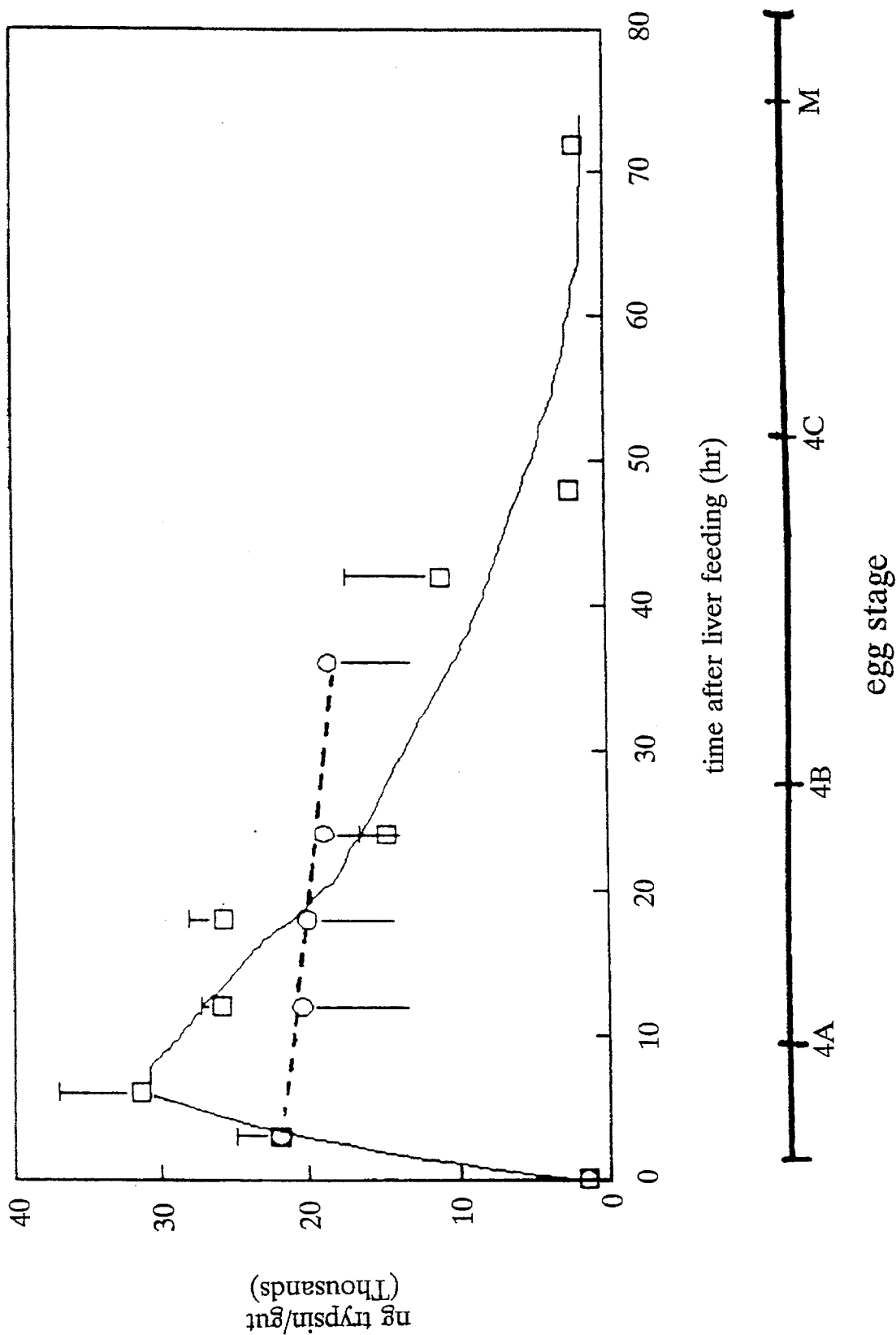
FIG. 2. Comparison between the amount of trypsin in the gut (µg/gut) and follicle development in the ovary at different times after liver feeding (0 hr). Egg stages are according to Pappas and Fraenkel (1978).

After a protein meal a steep rise in trypsin biosynthesis was observed reaching a peak at 6 hours and then declined to a minimum at 72 hours (FIG. 2). Egg development followed trypsin biosynthesis in the midgut (FIG. 2). In the males, cycles of increase and decrease in trypsin biosynthesis after a liver meal are less pronounced than in the female. At 96 hours after the eggs descended into the uterus, trypsin biosynthesis also increased. Thus, trypsin synthesis is cyclical and closely correlated with oocyte-development. Since chymotrypsin-like enzymes activity is less than 5% of trypsin-like activity no attempt was made to follow their biosynthesis.

EXAMPLE 2—Role of the Ovary in Modulating Trypsin Biosynthesis

Injection of a crude extract of ovaries (2 to 5 equivalents; 4C stage) after acid treatment into 4-day-old females immediately before a liver meal, inhibited 50% of trypsin biosynthesis 6 hours later when compared with controls. In ovariectomized flies the level of trypsin-like enzymes remains at a higher level, whereas, in sham operated or untreated controls, trypsin biosynthesis drops rapidly (FIG. 2). The initial increase in trypsin biosynthesis in ovariectomized females is less pronounced than in controls, and could be due to the operation. These results indicate that the ovary modulates trypsin biosynthesis in the fly.

EXAMPLE 3—HPLC Purification of Neb-TMOF

Figure 3:
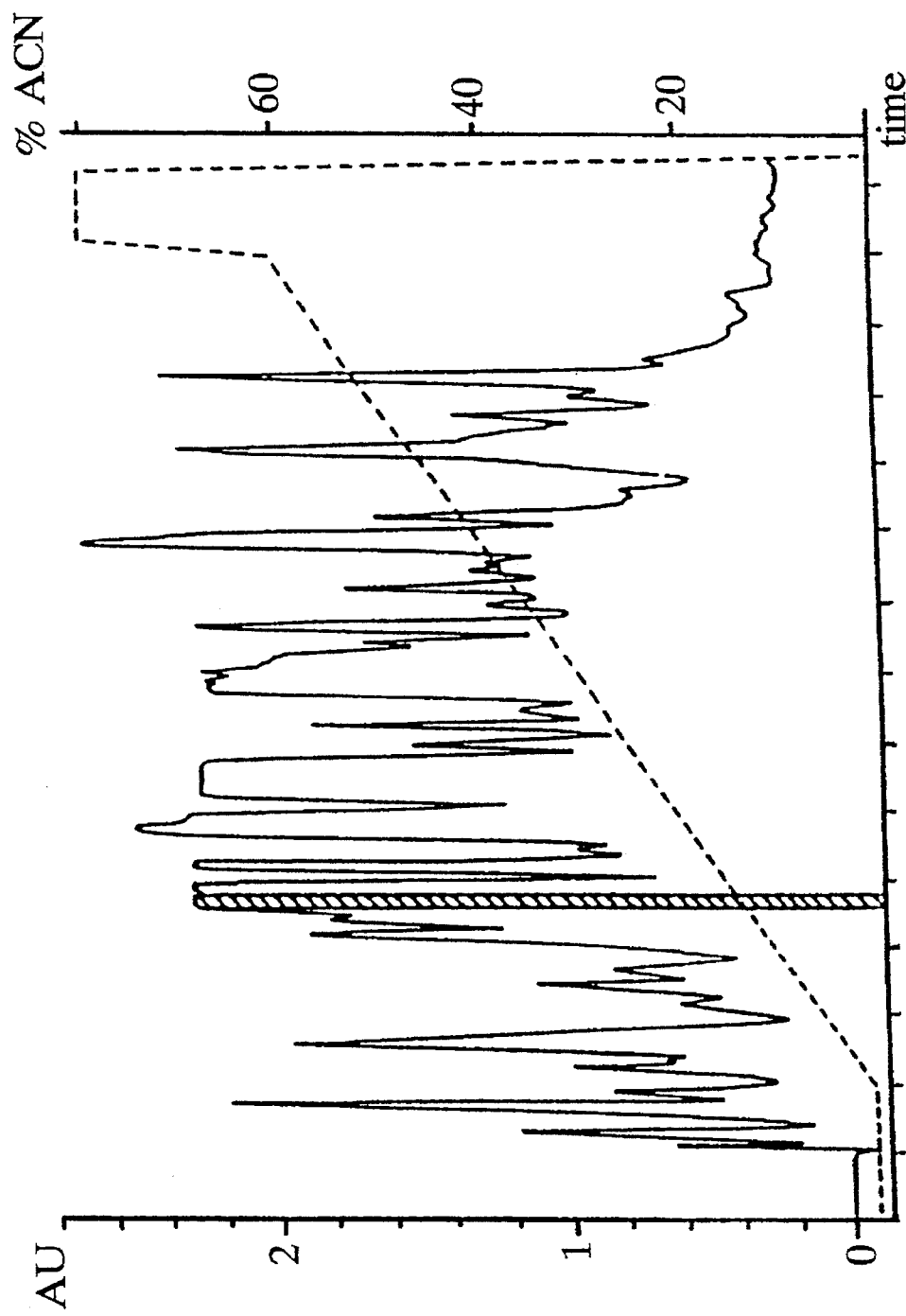
FIG. 3. First $C_{18}$ column (Deltapak) chromatography of 1,000 ovaries. The hatched area represents inhibition of oocyte development and trypsin biosynthesis.
Figure 4:
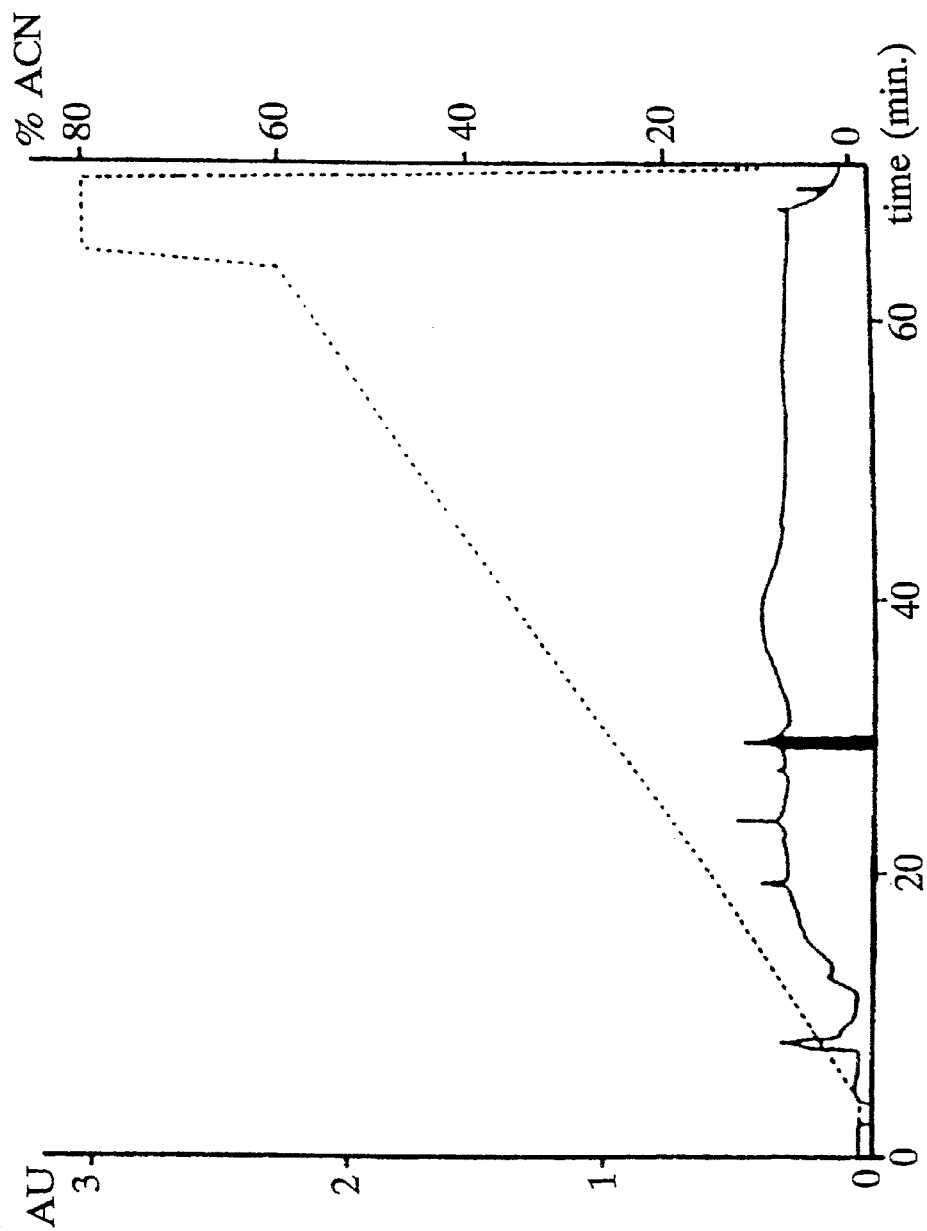
FIG. 4. Last HPLC-purification step (v) using $C_{18}$ column. Neb-TMOF was eluted at 25.6% acetonitrile. The diode array scan indicates absorbance only at 214 nm.

Ten Megabond Elut columns were used to prepurify the ovarian extract. The fraction eluted with 50% acetonitrile-water, 0.1% TFA significantly inhibited oocyte growth at 2 ovary equivalents. After the first HPLC column, Neb-TMOF activity was eluted at 20–21% acetonitrile (fractions 25–27) (FIG. 3). Injection of 2 ovary equivalents caused significant inhibition ($P<0.003$) of oocyte growth at 24 hours and significant decrease in the amount of trypsin at 6 hours after liver feeding. To conserve Neb-TMOF, fractions were monitored from this step onwards only for the effect on trypsin biosynthesis. Neb-TMOF was then purified on $C_8$ and 2 phenyl columns eluted with acetonitrile 0.1% TFA. A third phenyl column was then eluted with acetonitrile 0.1% HFBA. During the 4 column purification steps, Neb-TMOF activity was found in fractions eluted at 8, 10, 18 and 26% acetonitrile, respectively. Inhibition of trypsin biosynthesis during the 5 column purification steps was 44, 38, 43, 44 and 20% ($P<0.05$) using 1.25, 3.7, 10, 10 and 38.5 ovary equivalents, respectively. After the fifth column (FIG. 4), the peptide showed apparent homogeneity and was sequenced. Because of losses of biological activity due to sample loss during the five step purification procedure, higher number of ovary equivalents were needed at the last step to inhibit trypsin biosynthesis.

EXAMPLE 4—Sequence Determination of the Purified Neb-TMOF

Automated Edman sequence analysis of the isolated Neb-TMOF yielded an ambiguous analysis even though it had been subjected to five stages of purification. Aliquots of the sample were then analyzed by mass spectrometric analyses. Molecular masses were measured at 695.3, 709.4, and 737.4 for the free acid, methyl ester, and acetylated peptide respectively. Portions of purified Neb-TMOF and the above derivatives were then subjected to microcapillary HPLC interfaced directly to the electrospray ionization source of a Finnigan triple quadrupole mass spectrometer. Collision activated dissociation mass spectra were obtained for the $(M+H)^+$ ions of the free acid, methyl ester and acetylated peptides. Interpretation of this data led to the proposed sequence, $NH_2$-Asn-Pro-Thr-Asn-Leu(Ile)-His-COOH. Leu and Ile have identical mass and cannot be distinguished under the experimental conditions employed. Data obtained form the automated Edman sequence analysis was used to assign the fifth residue as leucine. The peptide $NH_2$-Asn-Pro-Thr-Asn-Leu-His-COOH was then synthesized, purified on reversed phase $C_{18}$ column and subjected to amino acid analysis which confirmed its primary structure. The synthetic hormone coeluted with the natural Neb-TMOF and was used in the biological studies.

EXAMPLE 5—Activity of the Synthetic Peptide, Dose Response and Mode of Action

Figure 5:
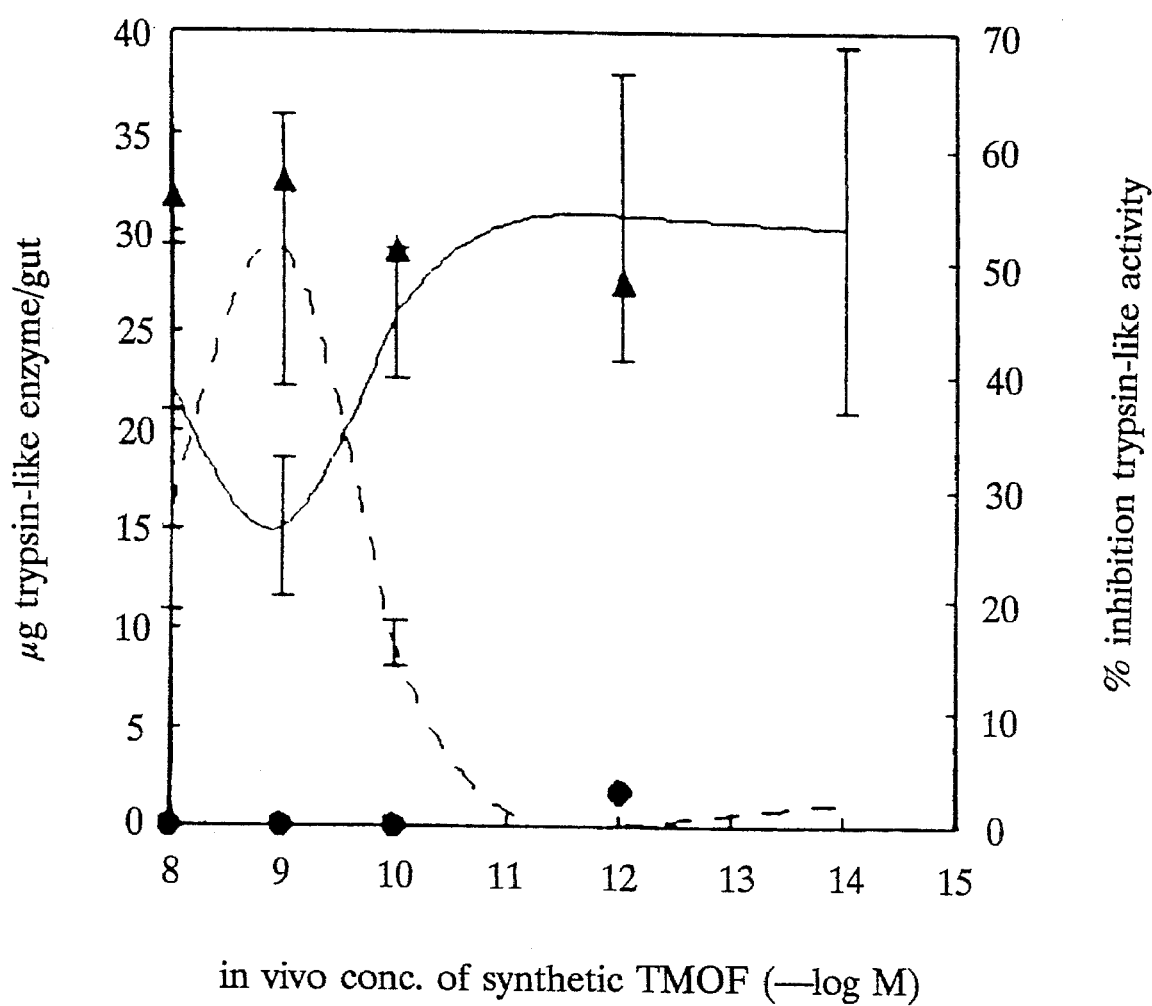
FIG. 5. Inhibition of trypsin biosynthesis in the gut by different doses of synthetic Neb-TMOF (- - -). Significant inhibition (- - -) ($P<0.05$) was obtained in vivo at concentrations of $10^{-8}$M and $10^{-9}$M.
Figure 6:
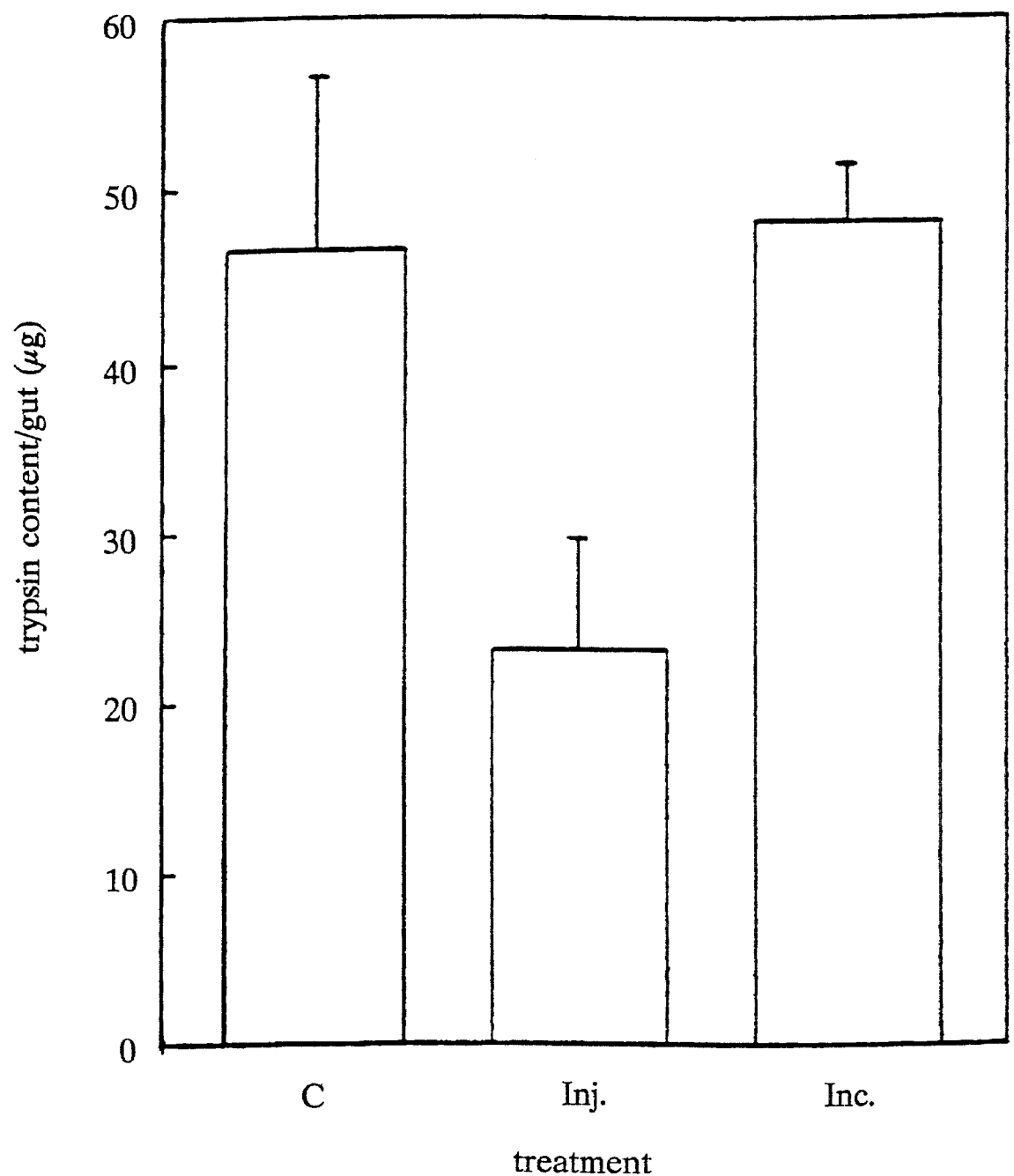
FIG. 6. Comparison between the effect of Neb-TMOF ($10^{-9}$M) on flies by: injection (inj), adding TMOF to the incubation medium (inc), or injecting flies with water (controls C).

To calculate the concentration of Neb-TMOF in the hemolymph after injection, we estimated that Neobellieria has 20 μl of hemolymph, which corresponds to 25% of the total weight of the fly. Injection of Neb-TMOF at concentrations of $10^{-8}$ and $10^{-9}$M into 4-day-old females resulted in a 35% and 60% inhibition of trypsin biosynthesis (FIG. 5). No inhibition was detected at concentrations of $10^{-11}$M. To find out if Neb-TMOF interferes with the conversion of $[^3H]DFP$ to $[^3H]DIP$-trypsin derivatives, guts were removed from flies 6 hours after a liver meal, homogenized, centrifuged and the supernatant incubated for 18 hours at 4° C. in the presence and absence of Neb-TMOF. No reduction in $[^3H]DIP$-trypsin derivatives was observed when compared with the controls (FIG. 6). To find out whether Neb-TMOF inhibits the de novo biosynthesis of trypsin, four-day-old females were injected with Neb-TMOF (final concentration $10^{-9}$M) and then fed a liver meal. Guts were removed 6 h later, homogenized, centrifuged, and supernatants incubated with $[^3H]DFP$ for 18 h at 4° C. and analyzed for $[^3H]DIP$-trypsin-like derivatives. A 51% reduction in trypsin-like enzymes was observed after injection of $10^{-9}$M Neb-TMOF as compared with controls (FIG. 6). These experiments demonstrate that Neb-TMOF inhibits trypsin biosynthesis and not trypsin activity as soybean trypsin inhibitor, N-tosyl-L-lysine chloromethyl ketone (TLCK), which bind to the active site of trypsin and inhibit enzyme activity.

EXAMPLE 6—Inhibition of Vitellogenin Synthesis by Neb-TMOF

Figure 7:
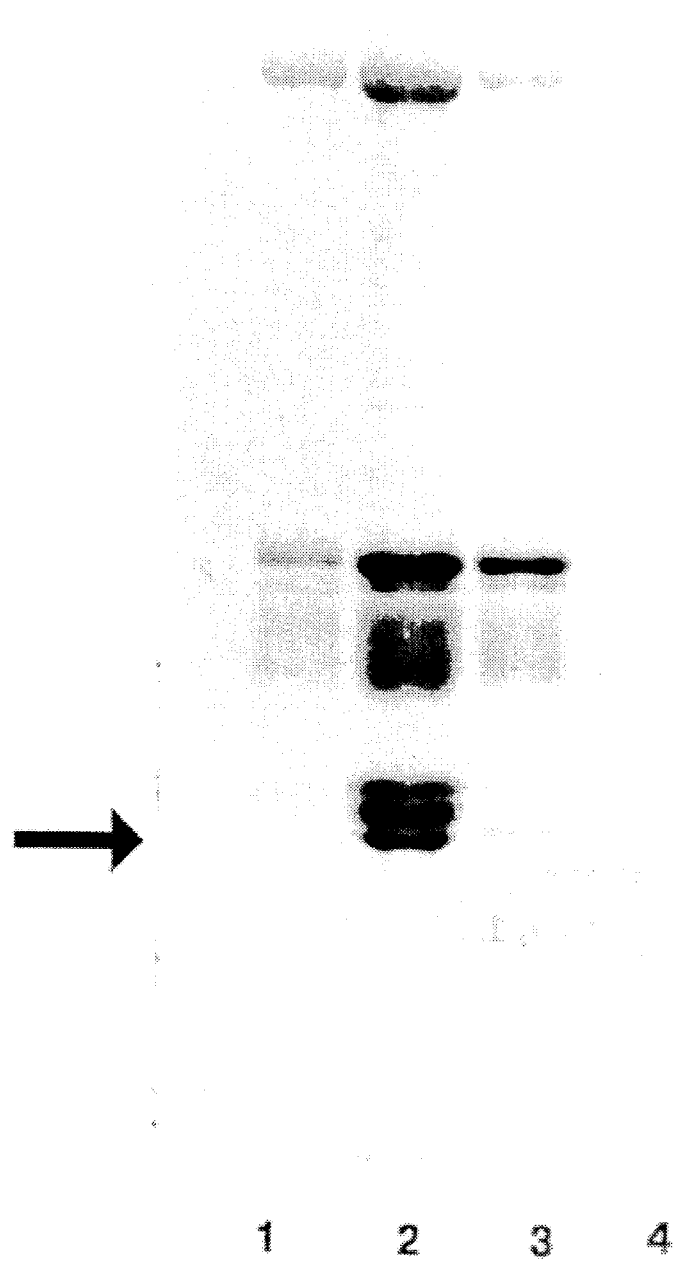
FIG. 7. Effect of Neb-TMOF on vitellogenin biosynthesis in flies. Females were injected with Neb-TMOF ($10^{-9}$M) and hemolymph (0.5 µl) was assayed for vitellogenin subunits using SDS-PAGE (5–15% gradient). Lane (1) Male's hemolymph; Lane (2) Hemolymph of control females; Lane (3) Hemolymph of Neb-TMOF injected females; Lane (4) Standards: phosphorylase b (94 kDa), Bovine Serum Albumin (67 kDa), Ovalbumin (43 kDa), Carbonic Anhydrase (30 kDa), Soybean trypsin inhibitor (20.1 kDa) and α-lactalbumin (14.4 kDa).

Four-day-old females were injected with synthetic Neb-TMOF at final concentration of $10^{-9}$M. Twenty-four hours later, hemolymph was collected and subjected to PAGE. As shown in FIG. 2, low level of vitellogenin was found in injected females as compared with non-injected controls. The three yolk polypeptides of vitellogenin were affected (FIG. 7). The decrease in vitellogenin in the hemolymph is probably due to the inhibition of trypsin biosynthesis and decrease in protein digestion in the gut. The Neb-TMOF can also affect the fat body, which is the major site of yolk polypeptide biosynthesis in Neobellieria.

EXAMPLE 7—Effect of Neb-TMOF on Ecdysteroid Synthesis

In addition to the direct effect of Neb-TMOF (SEQ ID NO. 1) on trypsin-like biosynthesis in both adults and larvae and the indirect effect of the peptide on oocyte growth, we observed activity of the subject peptide on ecdysteroid, e.g., ecdysone, biosynthesis and/or release. In insects, ecdysteroids are well known steroid hormones responsible for controlling processes involved in activation of genes for cuticle formation, stimulation of vitellogenin synthesis by the fat body, spermatocyte growth, and induction of diapause. The role of ecdysteroids in reproduction, especially in Diptera, is well known, and ecdysteroids were proved to initiate the synthesis of the female specific vitellogenin in males by injection of *Neobellieria bullata* (Huybrechts and De Loof, 1977).

The peptide of the subject invention was demonstrated to inhibit in vitro ecdysone biosynthesis by the ring glands of larvae of the flesh flies Calliphora and Neobellieria in a dose-dependent manner. The $EC_{50}$ was shown to be $5\times10^{-9}$M. More than 98% of ecdysone biosynthesis was inhibited at $10^{-7}$M. This activity is called prothoracico-inhibiting activity (PTIH). The PTIH effect by Neb-TMOF was shown to be immediate and reversible. A ten picomole quantity of the peptide per larva reduces in vivo the ecdysteroid titer by up to a factor of four within 18 hours.

Further recent studies showed the existence of the subject peptide in larvae and pupae of the flesh files. Thus, the subject peptide can have important physiological roles in ecdysteroid regulation and, hence, an effect on molting, growth, and gametogenesis. Because of the role of ecdysteroids on vitellogenin synthesis by the fat body, the inhibiting effect of Neb-TMOF on oocyte growth can be multiple. First, the supply of amino acids for vitellogenin production is prohibited by Neb-TMOF's effect on inhibiting digestion. Second, Neb-TMOF can arrest synthesis of ecdysone, the trigger for vitellogenin synthesis.

It should be understood that the examples and embodiments described herein are for illustrative purposes only and that various modifications or changes in light thereof will be suggested to persons skilled in the art and are to be included within the spirit and purview of this application and the scope of the appended claims.

References

Patents:

Borovsky, D., D. A. Carlson, U.S. Pat. No. 5,011,909, issued Apr. 30, 1991.

Borovsky, D., D. A. Carlson, U.S. Pat. No. 5,130,253, issued Jul. 14, 1992.

Publications

Adams, T. S., A. M. Hintz, J. G. Pomonis (1968) "Oostatic hormone production in Houseflies, *Musca domestica* with developing ovaries," *J. Insect Physiol.* 14:983–993.

Adams, T. S. (1976) "The ovaries, ring gland and neurosecretion during the second gonotrophic cycle in the housefly, *Musca domestica,*" *Gen. Comp. Endocrinol.* 30:69– 76.

Borovsky, D., B. R. Thomas, D. A. Carlson, L. R. Whisenton, M. S. Fuchs (1985) "Juvenile hormone and 20-hydroxyecdysone as primary and secondary stimuli of vitellogenesis in *Aedes aegypti,*" *Arch. Insect Biochem. Physiol.* 2:75–90.

Borovsky, D., Y. Schlein (1988) "Quantitative determination of trypsinlike and chymotrypsinlike enzymes in insects," *Arch. Insect Biochem. Physiol.* 8:249–260.

Borovsky, D., D. A. Carlson, P. R. Griffin, P. R., J. Shabanowitz, D. F. Hunt (1990) "Mosquito oostatic factor: a novel decapeptide modulating trypsin-like enzyme biosynthesis in the midgut," *FASEB J.* 4:3015–3020.

Borovsky, D., D. A. Carlson, I. Ujváry (1992a) "In vivo and in vitro biosynthesis and metabolism of methyl farnesoate, juvenile hormone III and juvenile hormone III acid in the mosquito *Aedes aegypti,*" *J. Med. Ent.* 29:619–629.

Borovsky, D., C. A. Powell, D. A. Carlson (1992b) "Development of specific RIA and ELISA to study trypsin modulating oostatic factor in mosquitoes," *Arch. Insect Biochem. Physiol.* 21:13–21.

Borovsky, D., D. A. Carlson, P. R. Griffin, J. Shabanowitz, D. F. Hunt (1993a) "Mass spectrometry and characterization of *Aedes aegypti* trypsin modulating oostatic factor (TMOF) and its analogs," *Insect Biochem. Mol. Biol.* 27:703–712.

Borovsky, D., D. A. Carlson, P. R. Griffin, J. Shabanowitz, D. F. Hunt (1993c) "Sequencing and characterization of *Aedes aegypti* trypsin modulating oostatic factor," In Borovsky, D., A. Spielman (eds) *Host Regulated Developmental mechanisms in Vector Arthropods,* Proceedings of the Third Symposium, University of Florida, Vero Beach, Fla., USA, pp. 36–47.

Borovsky, D., Q. Song, M. Ma, D.A. Carlson (1993d) "Biosynthesis, secretion, and cytoimmunochemistry of trypsin modulating oostatic factor of *Aedes aegypti,*" *Arch. Insect Biochem. Physiol.* (In press).

Domson, J., C. M. Kearney, M. E. Hilf, W. D. Davison (1991) "Systemic expression of a bacterial gene by a tobacco mosaic virus-based vector," *PNAS (Genetics)* 88:7204–7208.

Girardie, J., A. Girardie, J.-C. Huet, J.-C. Pernollet (1989) "Amino acid sequence of locust neuroparsins," *FEBS Letters* 245:4–8.

Goltzene, F., M. Lageaux, M. Charlet, J. A. Hoffman (1978) "The follicle cell epithelium of maturing ovaries of *Locusta migratoria*: a new biosynthetic tissue for ecdysone," *Hoppe-Seyler's Z. Physiol. Chem.* 359:1427–1434.

Hagedorn, H. H., J. D. O'Connor, M. S. Fuchs, B. Sage,

D. A Schlaeger, M. K Bohm (1975) "The ovary as a source of alpha-ecdysone in an adult mosquito," *Proc. Natl. Acad. Sci USA* 72:3255–3259.

Hanaoka, K., H. H. Hagedorn (1980) "Brain hormone control of ecdysone secretion by the ovary in mosquito," In *Progress in Ecdysone Research*, Hoffman, J. A. (ed.), Elsevier/North Holland, Amsterdam, pp. 467–479.

Harrap, K. A., C. C. Payne, J. S. Robertson (1977) *Virology* 79:14–31.

Hunt, D. F., J. Shabanowitz, J. R. Yates, III, N. Z. Zhu, D. H. Russell, M. E. Castro (1987) "Tandem Quadrupole Fourier-Transform Mass Spectrometry of Oligopeptides and Small Proteins," *Proc. Natl. Acad. Sci. USA* 84:620–623.

Huybrechts, R., A. De Loof (1977) "Induction of vitellogenin synthesis in male *Sarcophaga bullata* by ecdysterone," *J. Insect Physiol.* 23:1359–1362.

Huybrechts, R., A. De Loof (1982) "Similarities in vitellogenin and control of vitellogenin synthesis within the genera Sarcophaga, Calliphora, phormia and Lucilia (Diptera)," *Comp. Biochem. Physiol.* 72B:339–344.

Laemmli, U. K. (1970) "Cleavage of structural proteins during the assembly of the head of the bacteriophage T4," *Nature* 227:680–685.

Maniatis T., E. F. Fritsch, J. Sambrook (1982) *Molecular Cloning: A Laboratory Manual*, Cold Spring Harbor Laboratory, New York.

Merrifield (1963) *J. Amer. Chem. Soc.* 85:2149–2154 and Merrifield (1965) *Science* 150:178– 185.

Tarr, G. A. (1977) In *Methods in Enzymol*, Enzyme Structure, Part E (Hirs, C. H. W., S. N. Timashef, eds.), Vol. 47, pp. 335, 357.

Smith, G., M. D. Summers (1978) *Virology* 89:517–527.

Smith, G., M. D. Summers (1979) *J. Virology* 30:828–838.

Smith, G., M. D. Summers [1981]*J. Virol.* 39:125–137.

Volkman, L. E., M. D. Summers [1975]*J. Virol.* 16:1630–1637.

Woodhead, A. P., B. Stay, S. L. Seidel, M. A. Khan, S. S. Tobe (1989) "Primary structure of four allatostatins: Neuropeptide inhibitors of juvenile hormone synthesis," *Proc. Natl. Acad. Sci USA* 86:5997–6001.

We claim:

1. A substantially pure peptide having the amino acid sequence shown in SEQ ID NO. 1.

2. The peptide, according to claim 1, wherein the N-terminus of said peptide is acetylated.

3. The peptide, according to claim 1, wherein the C-terminus of said peptide is amidated.

4. The peptide, according to claim 1, comprising a D-amino acid.

5. The peptide, according to claim 1, wherein said peptide is bound to a lipid.

6. A pesticide composition comprising a peptide and a carrier, wherein said peptide has the amino acid sequence shown in SEQ ID NO. 1.

7. The pesticide, according to claim 6, wherein the C-terminus of said peptide is amidated.

8. The pesticide, according to claim 6, wherein the N-terminus of said peptide is acetylated.

9. The pesticide, according to claim 6, wherein said peptide is bound to a lipid.

* * * * *

UNITED STATES PATENT AND TRADEMARK OFFICE
CERTIFICATE OF CORRECTION

PATENT NO. : 5,459,130
DATED : October 17, 1995
INVENTOR(S) : Dov Borovsky, et al It is certified that error appears in the above-indentified patent and that said Letters Patent is hereby corrected as shown below:

Column 1:  line 27: "Aeries" should read --Aedes--.
Column 4:  line 46: "furniferana" should read --fumiferana--; line 52: "furniferana" should read --fumiferana--.
Column 5:  line 35: "plant pan" should read --plant part--.
Column 6:  line 17: "Fries" should read --Flies--; line 37: "convened" should read --converted--.
Column 11: lines 31-32: "5 x 10-$_9$M." should read --5 x 10$^{-9}$ M.--.

Signed and Sealed this

Fifth Day of March, 1996

Attest:

BRUCE LEHMAN

Attesting Officer   Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Asn  Pro  Thr  Asn  Leu  His
    1                   5